(12) United States Patent
Lalleman

(10) Patent No.: US 8,888,866 B2
(45) Date of Patent: Nov. 18, 2014

(54) DYEING PROCESS USING A NATURAL DYE ON KERATIN FIBRES THAT HAVE UNDERGONE PERMANENT RESHAPING

(75) Inventor: Boris Lalleman, Paris (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 14/234,124

(22) PCT Filed: Jul. 20, 2012

(86) PCT No.: PCT/EP2012/064265
§ 371 (c)(1),
(2), (4) Date: Jan. 21, 2014

(87) PCT Pub. No.: WO2013/011116
PCT Pub. Date: Jan. 24, 2013

(65) Prior Publication Data
US 2014/0150185 A1    Jun. 5, 2014

Related U.S. Application Data

(60) Provisional application No. 61/528,696, filed on Aug. 29, 2011, provisional application No. 61/528,700, filed on Aug. 29, 2011.

(30) Foreign Application Priority Data

Jul. 21, 2011  (FR) ..................................... 11 56620
Jul. 21, 2011  (FR) ..................................... 11 56621

(51) Int. Cl.
*A61Q 5/10*   (2006.01)
*A61K 8/97*   (2006.01)

(52) U.S. Cl.
CPC .... *A61K 8/97* (2013.01); *A61Q 5/10* (2013.01)
USPC ............. 8/405; 8/426; 8/576; 8/579; 8/637.1; 8/646; 8/101; 8/111; 132/202; 132/208

(58) Field of Classification Search
USPC .......... 8/405, 426, 576, 579, 637.1, 646, 101, 8/111; 132/202, 208
See application file for complete search history.

(56) References Cited

U.S. PATENT DOCUMENTS

2005/0005368 A1   1/2005   Plos
2009/0249563 A1   10/2009  Greaves

FOREIGN PATENT DOCUMENTS

| FR | 2 942 594 A1 | 9/2010 | |
|---|---|---|---|
| JP | 9-87152 A | 3/1997 | |
| WO | 2011/020857 A2 | 2/2011 | |
| WO | WO 2011/020857 A2 * | 2/2011 | ............... A61Q 5/10 |

OTHER PUBLICATIONS

STIC Search Report dated May 5, 2014.*
International Preliminary Report on Patentability mailed Mar. 12, 2014, issued in International Application No. PCT/EP2012/064265, filed Jul. 20, 2012, 10 pages.
International Search Report and Written Opinion mailed Mar. 12, 2014, issued in International Application No. PCT/EP2012/064265, filed Jul. 20, 2012, 14 pages.
"Logona Pflanzen-Haarfarben," <http://www.aim-naturprodukte.com/naturprodukte/pflanzenhaarfarben.html> [retrieved Mar. 22, 2012], 1 page.
"Pflanzenhaarfarben—Übersicht," <http://beautyjunkies.inbeauty.de/w/index.php?title=Pflanzenhaarfarben_-_%c3%9cbersicht> [retrieved Mar. 22, 2012], 4 pages.

* cited by examiner

*Primary Examiner* — Eisa Elhilo
(74) *Attorney, Agent, or Firm* — Christensen O'Connor Johnson Kindness PLLC

(57) ABSTRACT

Dyeing process using a natural dye on keratin fibers that have undergone permanent reshaping The present invention relates to a process for dyeing keratin fibers, in particular human keratin fibers such as the hair, in which: a) an aqueous alkaline composition comprising one or more alkaline agents in an amount such that the pH of the composition is greater than at least 10 is applied to the said fibers, or a reducing composition comprising one or more reducing agents and then an oxidizing composition are applied to the said fibers, b) the said fibers are optionally rinsed, c) optionally, the treatment is neutralized, and the fibers are washed with shampoo and rinsed, d) optionally, the fibers are dried or left to dry, e) a dye composition comprising, in a cosmetically acceptable medium, one or more natural dyes is applied to the said fibers, f) optionally, the fibers are washed and rinsed, g) the fibers are dried or left to dry.

17 Claims, No Drawings

DYEING PROCESS USING A NATURAL DYE ON KERATIN FIBRES THAT HAVE UNDERGONE PERMANENT RESHAPING

The present invention relates to a process for dyeing keratin fibres, in particular human keratin fibres such as the hair, which have previously undergone a permanent reshaping process following the application of a reducing composition and then an oxidizing composition or following the application of an alkaline composition, using a dye composition comprising, in a cosmetically acceptable medium, one or more natural dyes.

In the field of haircare, it is common to wish to perform a permanent shaping or permanent reshaping step by straightening or relaxing and a dyeing step within a short interval, the shaping or reshaping operation being performed during the first step, the desire moreover being to perform these two treatments immediately one after the other, in particular when these treatments are performed in a hairstyling salon in order especially to avoid two consecutive visits. However, it has been observed that such processes cause damage to the keratin fibres.

Specifically, one of the standard perming processes consists in working in two steps, the first consisting in reducing the disulfide bridges present in the keratin fibre, using a reducing agent. Once these disulfide bridges have been reduced, the hair is then shaped in the desired manner. This shaping step may consist in curling the hair or in straightening it, the result being dependent on the means used to achieve the placing under tension.

This step of placing under tension may be performed before, during or after the application of the reducing composition. Once this first step has been performed, an oxidation step is necessary in order to recreate the disulfide bridges and to stabilize the shape obtained. This operation is usually performed in an oxidizing medium.

Moreover, another process for permanently reshaping the hair, which is applicable essentially in the case of relaxing, usually consists in applying to the head of hair, while straightening it, a concentrated solution of an alkali metal hydroxide. During this operation, the keratin fibre is relatively damaged because it is partially dissolved in the alkaline solution. Once this treatment has been performed, the hair is rinsed.

It is thus clear that after treatments of this type, the keratin fibre is in a relatively damaged and embrittled state, and performing a subsequent dyeing step represents a further risk of degradation, this risk being all the more pronounced since lightening conditions are generally used in order to obtain good coverage of grey hair.

Specifically, most of the dyeing processes that afford a good level of coverage of grey hair are performed in the presence of an oxidizing agent in an alkaline medium. Furthermore, these conditions are all the more harsh since the desired degree of coverage of the grey hair in a head of hair is substantial.

Moreover, it is known practice to dye keratin fibres and in particular human hair with dye compositions containing oxidation dye precursors, which are generally known as oxidation bases, such as ortho- or para-phenylenediamines, ortho- or para-aminophenols and heterocyclic compounds. These oxidation bases are generally combined with couplers. These bases and couplers are colourless or weakly coloured compounds, which, when combined with oxidizing products, may give rise to coloured compounds by a process of oxidative condensation.

This type of oxidation dyeing makes it possible to obtain permanent colorations, but it results in degradation of the keratin fibres due to the use of oxidizing agents.

It is also known practice to dye keratin fibres and in particular human hair with dye compositions containing direct dyes. The standard dyes that are used are, in particular, dyes of the nitrobenzene, anthraquinone, nitropyridine, azo, xanthene, acridine, azine or triarylmethane type, or natural dyes.

These dyes may be nonionic, anionic, cationic or amphoteric. These dyes are coloured and colouring molecules that have affinity for keratin fibres.

The majority of the direct dyes used have sufficient solubility in aqueous medium, and numerous dye supports suitable for receiving them now exist.

These compositions containing one or more direct dyes are applied to keratin fibres for a time necessary to obtain the desired coloration, and are then rinsed out.

However, the colorations resulting therefrom are particularly chromatic colorations, but are, however, only temporary or semi-permanent since the nature of the interactions that bind the direct dyes to the keratin fibre and their desorption from the surface and/or the core of the fibre are responsible for their weak dyeing power and their poor fastness with respect to washing.

Moreover, the colorations may also be performed in the presence of oxidizing agents under lightening conditions, thus leading to damage of the keratin fibres.

The aim of the present invention is thus especially to propose a dyeing process performed subsequent to a process for the permanent reshaping of keratin fibres, which not only affords a good level of coverage of the fibres, but also offers powerful and fast colorations, and does not substantially contribute towards new degradation of the treated fibres.

One subject of the present invention is thus especially a process for dyeing keratin fibres, in particular human keratin fibres such as the hair, in which:

a) an aqueous alkaline composition comprising one or more alkaline agents in an amount such that the pH of the composition is greater than at least 10 is applied to the said fibres, or a reducing composition comprising one or more reducing agents and then an oxidizing composition are applied to the said fibres, b) the said fibres are optionally rinsed, c) optionally, the treatment is neutralized, and the fibres are washed with shampoo and rinsed, d) optionally, the fibres are dried or left to dry, e) a dye composition comprising, in a cosmetically acceptable medium, one or more natural dyes is applied to the said fibres, f) optionally, the fibres are washed and rinsed, g) the fibres are dried or left to dry.

In accordance with the present invention, the dyeing process is performed on keratin fibres that have undergone beforehand either a permanent reshaping process following the application of a reducing composition comprising one or more reducing agents and an oxidizing composition, or a permanent reshaping process by straightening or relaxing performed after the application of an alkaline cosmetic composition with a pH of at least 10. In other words, the dye composition according to the invention may be applied to keratin fibres without waiting, just after performing the permanent reshaping process and the optional rinsing, neutralizing, washing and drying steps, or in a delayed manner.

The dyeing process according to the invention leads to powerful, chromatic colorations that are fast, in particular with respect to shampoos and ultraviolet and visible radiation.

Furthermore, the coverage of grey hair is very satisfactory.

Other characteristics, aspects, subjects and advantages of the present invention will emerge even more clearly on reading the description and the examples that follow.

In accordance with the present invention, the dyeing process uses a dye composition comprising, in a cosmetically acceptable medium, one or more natural dyes.

The term "natural dye" means any dye or dye precursor that is naturally occurring and that is produced either by extraction (and possible purification) from a plant matrix optionally in the presence of natural compounds such as ash or ammonia, or via chemical synthesis.

Natural dyes that may be mentioned include lawsone and henna, curcumin, chlorophylline, alizarin, kermesic acid, purpurin, purpurogallin, indigo, Tyrian purple, sorghum, carminic acid, catechin, epicatechin, juglone, bixin, betanin, quercetin, chromene dyes and chroman dyes, and laccaic acids.

Preferably, the natural dyes used in the invention are chosen from curcumin, chlorophylline, chromene dyes, chroman dyes and laccaic acids.

According to the invention, the terms "chromene dye" and "chroman dye" mean dyes which comprise in their structure at least one bicycle of formula (A) below:

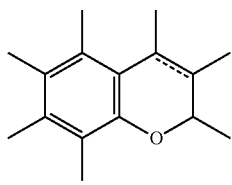
A the endocyclic bond ---- representing a carbon-carbon single bond or a carbon-carbon double bond, as illustrated by formula A1 denoting the chromene family and formula A2 denoting the chroman family below:

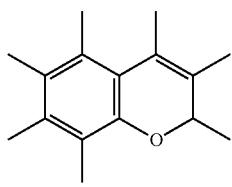
A1

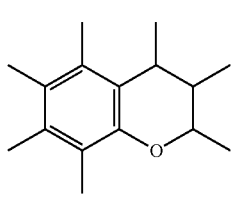
A2

More particularly, the dyes having in their structure a bicycle of formula (A) are chosen from the dyes having the following formulae:

formula (I), comprising in its structure the bicycle of formula A2,

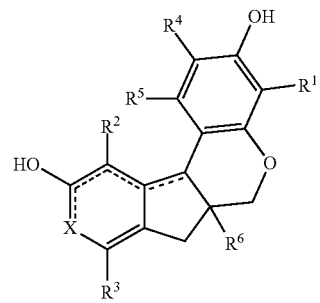
(I)

in which:

---- represents a carbon-carbon single bond or a carbon-carbon double bond, the sequence of these bonds ---- denotes two carbon-carbon single bonds and two carbon-carbon double bonds, the said bonds being conjugated, X represents a group:

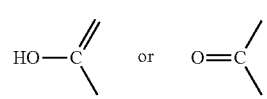

$R^1$, $R^2$, $R^3$, $R^4$, $R^5$ and $R^6$, which may be identical or different, represent, independently of each other, a hydrogen atom, a hydroxyl group, an optionally substituted alkyl group, an optionally substituted alkoxy group or an optionally substituted acyloxy group, and also the tautomeric and/or mesomeric forms thereof, the stereoisomers thereof, the addition salts thereof with a cosmetically acceptable acid or base, and the hydrates thereof, and formula (II), comprising in its structure the bicycle of formula A1:

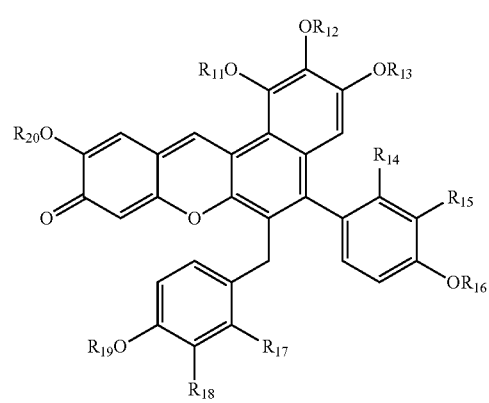
(II)

in which:

$R_{11}$, $R_{12}$, $R_{13}$, $R_{16}$, $R_{19}$ and $R_{20}$, which may be identical or different, represent, independently of each other, a hydrogen atom or a $C_1$-$C_4$ alkyl radical, $R_{14}$, $R_{15}$, $R_{17}$ and $R_{18}$, which may be identical or different, represent, independently of each other, a hydrogen atom, a hydroxyl radical or a $C_1$-$C_4$ alkoxy radical, and also the tautomeric and/or mesomeric forms thereof, the stereoisomers thereof, the addition salts thereof with a cosmetically acceptable acid or base, and the hydrates thereof.

As regards the dyes of formula (I) as defined previously, they may be in two tautomeric forms noted (Ia) and (Ib):

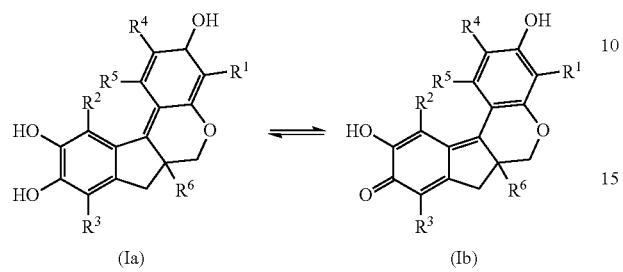

The alkyl radicals mentioned in the preceding definitions of the substituents are linear or branched, saturated hydrocarbon-based radicals, generally of $C_1$-$C_{20}$, particularly of $C_1$-$C_{10}$ and preferably of $C_1$-$C_6$, such as methyl, ethyl, propyl, butyl, pentyl and hexyl.

The alkoxy radicals are alkyl-oxy radicals with alkyl as defined previously and preferably the alkoxy radicals are of $C_1$-$C_{10}$, such as methoxy, ethoxy, propoxy and butoxy.

The alkyl or alkoxy radicals, when they are optionally substituted, may be substituted with at least one substituent borne by at least one carbon atom, chosen from:
- a halogen atom;
- a hydroxyl group;
- a $C_1$-$C_2$ alkoxy radical;
- a $C_1$-$C_{10}$ alkoxycarbonyl radical;
- a $C_2$-$C_4$ (poly)hydroxyalkoxy radical;
- an amino radical;
- a 5- or 6-membered heterocycloalkyl radical;
- an optionally cationic 5- or 6-membered heteroaryl radical, preferentially imidazolium, optionally substituted with a ($C_1$-$C_4$)alkyl radical, preferentially methyl;
- an amino radical substituted with one or two identical or different $C_1$-$C_6$ alkyl radicals, optionally carrying at least:
  - one hydroxyl group,
  - one amino group optionally substituted with one or two optionally substituted $C_1$-$C_3$ alkyl radicals, the said alkyl radicals possibly forming with the nitrogen atom to which they are attached a saturated or unsaturated, optionally substituted 5- to 7-membered heterocycle, optionally comprising at least one other heteroatom identical to or different from nitrogen,
  - a quaternary ammonium group —N$^+$R'R"R''', M$^-$ for which R', R" and R''', which may be identical or different, represent a hydrogen atom or a $C_1$-$C_4$ alkyl group; and M$^-$ represents the counterion of the organic or mineral acid or of the corresponding halide;
  - or one optionally cationic 5- or 6-membered heteroaryl radical, preferentially imidazolium, optionally substituted with a ($C_1$-$C_4$)alkyl radical, preferentially methyl;
- an acylamino radical (—NR—COR') in which the radical R is a hydrogen atom or a $C_1$-$C_4$ alkyl radical optionally bearing at least one hydroxyl group and the radical R' is a $C_1$-$C_2$ alkyl radical;
- a carbamoyl radical ((R)$_2$N—CO—) in which the radicals R, which may be identical or different, represent a hydrogen atom or a $C_1$-$C_4$ alkyl radical optionally bearing at least one hydroxyl group;
- an alkylsulfonylamino radical (R'SO$_2$—NR—) in which the radical R represents a hydrogen atom or a $C_1$-$C_4$ alkyl radical optionally bearing at least one hydroxyl group and the radical R' represents a $C_1$-$C_4$ alkyl radical or a phenyl radical;
- an amino sulfonyl radical ((R)$_2$N—SO$_2$—) in which the radicals R, which may be identical or different, represent a hydrogen atom or a $C_1$-$C_4$ alkyl radical optionally bearing at least one hydroxyl group;
- a carboxylic radical in acid or salified form (preferably with an alkali metal or a substituted or unsubstituted ammonium);
- a cyano group;
- a nitro group;
- a carboxyl or glycosylcarbonyl group;
- a phenylcarbonyloxy group optionally substituted with one or more hydroxyl groups;
- a glycosyloxy group; and
- a phenyl group optionally substituted with one or more hydroxyl groups.

The term "glycosyl radical" means a radical derived from a monosaccharide or polysaccharide.

Preferably, the alkyl or alkoxy radicals of formula (I) are unsubstituted.

According to one particular embodiment of the invention, the dyes of formula (I) comprise a radical $R^6$ representing a hydroxyl group.

Another particular embodiment of the invention concerns the dyes of formula (I), for which the radical $R^1$ represents a hydrogen atom or a hydroxyl group.

More particularly, the dyes of formula (I) are chosen from haematoxylin, haematin, brazilin and brazileine.

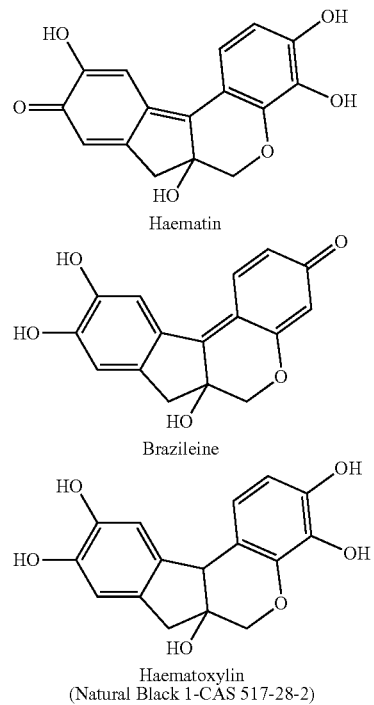

Haematin

Brazileine

Haematoxylin
(Natural Black 1-CAS 517-28-2)

-continued

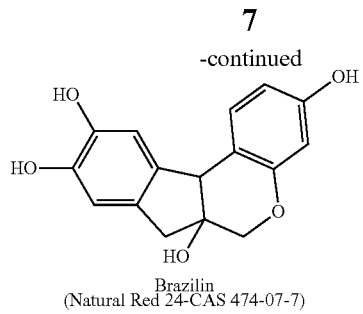

Brazilin
(Natural Red 24-CAS 474-07-7)

Brazileine is a conjugated form of a chroman compound of formula A2. The tautomeric structures (Ia) and (Ib) illustrated above are found in the scheme below.

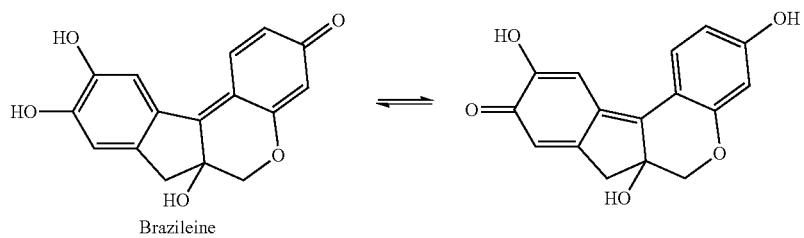

Brazileine

Among the haematoxylin/haematin and brazilin/brazileine dyes, examples that may be mentioned include haematoxylin (Natural Black 1 according to the INCI name) and brazilin (Natural Red 24 according to the INCI name), dyes of the indochroman family, which are commercially available. The latter dyes may exist in an oxidized form and may be obtained synthetically or by extraction of plants or vegetables known to be rich in these dyes.

The dyes of formula (I) may be used in the form of extracts. Use may be made of the following plant extracts (genus and species): *Haematoxylon campechianum, Haematoxylon brasiletto, Caesalpinia echinata, Caesalpinia sappan, Caesalpinia spinosa*, and *Caesalpina brasiliensis*.

The extracts are obtained by extracting the various plant parts, for instance the root, the wood, the bark or the leaves.

According to one particular embodiment of the invention, the natural dyes of formula (I) are obtained from logwood, pernambuco wood, sappan wood and Brazil wood.

The salts of the dyes of formulae (I) and (II) of the invention may be salts of cosmetically acceptable acids or bases.

The acids may be mineral or organic. Preferably, the acid is hydrochloric acid, which results in chlorides.

The bases may be inorganic or organic. In particular, the bases are alkali metal hydroxides such as sodium hydroxide, which leads to sodium salts.

Preferably, the dye(s) of formulae (I) and (II) included in the composition according to the invention are derived from plant extracts. Mixtures of plant extracts may also be used.

The natural extracts according to the invention may be in the form of powders or liquids. Preferably, the compositions are in powder form.

In a second variant, the natural dyes are chosen from laccaic acids.

For the purposes of the present invention, the term "laccaic acid" means a compound having in its structure a unit of the type:

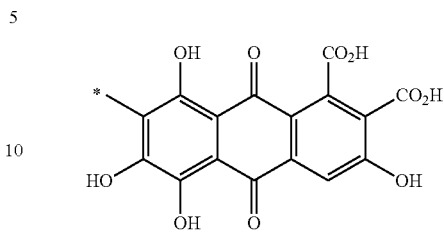

Preferably, the laccaic acids of the invention are of formula (III) below:

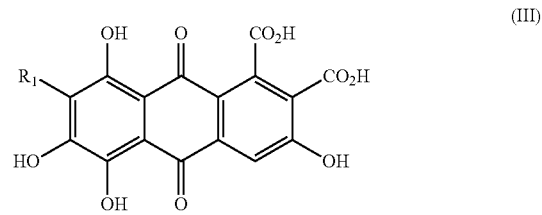

(III)

with $R_1$ denoting a phenyl radical substituted with at least one hydroxyl group, and preferably with a hydroxyl group that is advantageously in the ortho position relative to the bond attaching it to the fused rings.

Preferably, the radical $R_1$ comprises, besides a hydroxyl group, at least one group —$CH_2R_2$, $R_2$ denoting an acetamidomethyl group ($CH_3CONHCH_2$—), hydroxymethyl ($HOCH_2$—) or 2-aminoacetic acid ($HO_2C(NH_2)CH$—).

More preferentially, the laccaic acids of the invention are chosen from laccaic acid A, B or C, or mixtures thereof.

Laccaic acid A

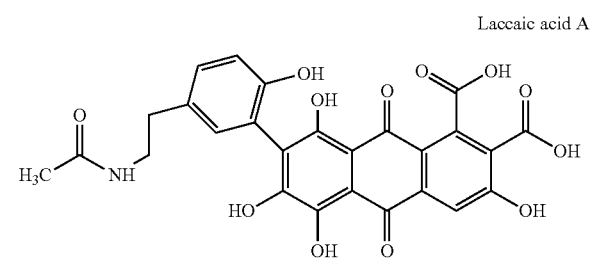

Laccaic acid B

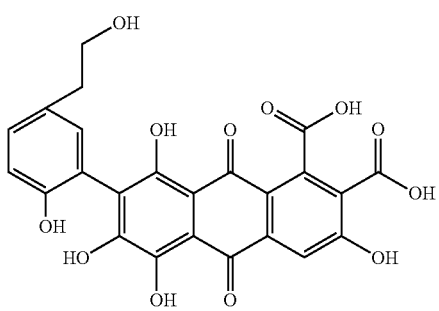

Laccaic acid C

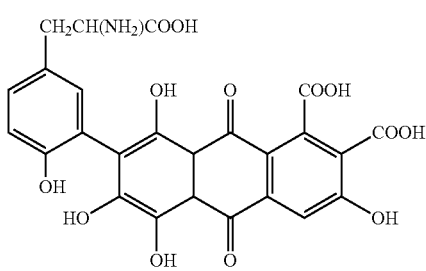

A laccaic acid according to the invention that may especially be used is the dye CI Natural Red 25, CI-75450, CAS-60687-93-6, which is often referred to as laccaic acid. This is a dye of natural origin originating from the secretions of an insect, *Coccus laccae* (Lacifer Lacca Kerr), which is generally found on the twigs of certain trees native to South-east Asia.

CI Natural Red 25 generally contains two major constituents in its composition: laccaic acid A and laccaic acid B. It may also contain a small amount of laccaic acid C.

It is obviously also possible to use the purified forms of the laccaic acids of formula (III).

Preferably, the natural dyes are chosen from haematoxylin, haematin, brazileine and brazilin, and mixtures thereof.

Even more preferentially, the natural dyes are chosen from haematin and brazileine.

The natural dye(s) may be present in the dye composition according to the present invention in a content ranging from 0.1% to 20% by weight, preferably in a content ranging from 0.2% to 10% by weight and even more preferentially in a content ranging from 0.5% to 5% by weight relative to the total weight of the composition.

Preferably, the dye composition may also contain one or more aromatic alcohols.

For the purposes of the present invention, the term "aromatic alcohol" means any compound, which is liquid at room temperature and atmospheric pressure, comprising at least one benzene or naphthalene ring and at least one alcohol function (OH) directly linked to the ring or linked to at least one substituent on the said ring. Preferably, the alcohol function is on a substituent of the benzene or naphthalene ring.

Among the aromatic alcohols that may be used in the dye composition, mention may be made in particular of:
benzyl alcohol,
benzoylisopropanol,
benzyl glycol,
phenylethanol,
dichlorobenzyl alcohol,
methylphenylbutanol,
phenoxyisopropanol,
phenylisohexanol,
phenylpropanol,
phenylethyl alcohol,
and mixtures thereof.

Preferably, the aromatic alcohol that may be used in the dye composition is chosen from benzyl alcohol, phenylpropanol and phenylethanol.

The cosmetically acceptable medium generally consists of water or of a mixture of water and of one or more common organic solvents.

Among the suitable solvents, mention may be made more particularly of non-aromatic alcohols such as ethyl alcohol, isopropyl alcohol, or glycols or glycol ethers, for instance ethylene glycol monomethyl, monoethyl or monobutyl ether, propylene glycol or ethers thereof, for instance propylene glycol monomethyl ether, butylene glycol, dipropylene glycol, and also diethylene glycol alkyl ethers, for instance diethylene glycol monoethyl ether or monobutyl ether, or alternatively polyols such as glycerol. Polyethylene glycols and polypropylene glycols, and mixtures of all these compounds, may also be used as solvent.

The common solvents described above, if they are present, usually represent from 0.1% to 15% by weight and more preferentially from 0.5% to 5% by weight relative to the total weight of the composition.

The pH of the composition is generally between 2.5 and 11 approximately and preferably between 2.7 and 10 approximately.

It may be adjusted to the desired value by means of acidifying or basifying agents.

Among the acidifying agents that may be mentioned, for example, are mineral or organic acids, for instance hydrochloric acid, orthophosphoric acid or sulfuric acid, carboxylic acids, for instance acetic acid, tartaric acid, citric acid and lactic acid, and sulfonic acids.

Mention may be made, among the basifying agents, by way of example, of aqueous ammonia, alkaline carbonates, alkanolamines, such as mono-, di- and triethanolamines, and their derivatives, sodium hydroxide, potassium hydroxide and the compounds of formula (IV) below:

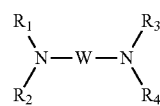

(IV)

in which W is a propylene residue optionally substituted with a hydroxyl group or a $C_1$-$C_6$ alkyl radical; and $R_1$, $R_2$, $R_3$ and $R_4$, which may be identical or different, represent a hydrogen atom or a $C_1$-$C_6$ alkyl or $C_1$-$C_6$ hydroxyalkyl radical.

The dye composition according to the invention may be used under lightening conditions.

The lightening of hair is evaluated by the "tone depth", which characterizes the degree or level of lightening. The notion of "tone" is based on the classification of natural shades, one tone separating each shade from the shade immediately following or preceding it. This definition and the classification of natural shades are well known to hairstyling professionals and are published in the book "Sciences des traitements capillaires [Hair treatment sciences]" by Charles Zviak, 1988, published by Masson, pp. 215 and 278.

The tone depths range from 1 (black) to 10 (light blond), one unit corresponding to one tone; the higher the figure, the lighter the shade.

Thus, the dye composition may also comprise one or more oxidizing agents chosen, for example, from hydrogen peroxide, urea peroxide, alkali metal bromates, persalts such as perborates and persulfates, and enzymes such as peroxidases and two-electron or four-electron oxidoreductases. The use of hydrogen peroxide is particularly preferred.

The dye composition in accordance with the present invention may also comprise one or more oxidation bases chosen from the oxidation bases conventionally used for oxidation dyeing, and among which mention may be made especially of para-phenylenediamines, bis(phenyl)alkylenediamines, para-aminophenols, ortho-aminophenols and heterocyclic bases, and the addition salts thereof with an acid or with an alkaline agent.

When they are used, the oxidation base(s) preferably represent from 0.001% to 20% by weight, and even more preferably from 0.01% to 10% by weight relative to the total weight of the composition.

When it is intended for oxidation dyeing, the composition according to the invention may also comprise one or more couplers so as to modify or to enrich with tints the shades obtained using the direct dyes and the oxidation base(s).

The couplers that may be used may be chosen from the couplers conventionally used in oxidation dyeing, and among which mention may be made especially of meta-phenylenediamines, meta-aminophenols, meta-diphenols and heterocyclic couplers, and the addition salts thereof with an acid or with an alkaline agent.

When they are present, the coupler(s) preferably represent(s) from 0.001% to 20% by weight and even more preferentially from 0.01% to 10% by weight relative to the total weight of the composition.

Thus, the dye composition may comprise one or more oxidation bases and/or couplers.

In general, the addition salts with an acid that can be used in the context of the compositions of the invention (oxidation bases and the couplers) are selected in particular from hydrochlorides, hydrobromides, sulfates, citrates, succinates, tartrates, tosylates, benzenesulfonates, lactates and acetates.

The addition salts with an alkaline agent that may be used in the context of the compositions of the invention (oxidation bases and couplers) are especially chosen from addition salts with alkali metals or alkaline-earth metals, with ammonia, with organic amines including alkanolamines and the compounds of formula (IV).

The cosmetic composition may also comprise one or more hydrophilic or organophilic clays.

Clays are silicates containing a cation that may be chosen from calcium, magnesium, aluminium, sodium, potassium and lithium cations, and mixtures thereof. The term "hydrophilic clay" means a clay that is capable of swelling in water; this clay swells in water and forms, after hydration, a colloidal dispersion.

Examples of such products that may be mentioned include clays of the smectite family such as montmorillonites, hectorites, bentonites, beidellites and saponites, and also of the family of vermiculites, stevensite and chlorites. These clays may be of natural or synthetic origin.

Hydrophilic clays that may be mentioned include smectites such as saponites, hectorites, montmorillonites, bentonites or beidellite and in particular synthetic hectorites (also known as laponites), for instance the products sold by the company Laporte under the names Laponite XLG, Laponite RD and Laponite RDS (these products are sodium magnesium silicates and in particular sodium lithium magnesium silicates); bentonites, for instance the product sold under the name Bentone HC by the company Rheox; magnesium aluminium silicates, which are especially hydrated, for instance the products sold by the company Vanderbilt Company under the names Veegum Ultra, Veegum HS and Veegum DGT, or alternatively calcium silicates and especially the product in synthetic form sold by the company under the name Micro-cel C.

The organophilic clays are clays modified with chemical compounds that make the clay capable of swelling in solvent media.

The organophilic clays are clays modified with a chemical compound chosen from quaternary amines, tertiary amines, amine acetates, imidazolines, amine soaps, fatty sulfates, alkyl aryl sulfonates and amine oxides, and mixtures thereof.

Organophilic clays that may be mentioned include quaternium-18 bentonites such as those sold under the names Bentone 3, Bentone 38 and Bentone 38V by the company Elementis, Tixogel VP by the company United Catalyst, and Claytone 34, Claytone 40 and Claytone XL by the company Southern Clay; stearalkonium bentonites such as those sold under the names Bentone 27V by the company Elementis, Tixogel LG by the company United Catalyst, and Claytone AF and Claytone APA by the company Southern Clay; quaternium-18/benzalkonium bentonites such as those sold under the names Claytone HT and Claytone PS by the company Southern Clay.

In particular, the dye composition may comprise one or more clays chosen from bentonite and laponite.

The cosmetic composition in accordance with the invention may also comprise one or more cosmetic adjuvants.

The cosmetic adjuvant(s) that are conventionally used in cosmetic compositions, especially for dyeing human keratin fibres, may be chosen from anionic, cationic, nonionic, amphoteric or zwitterionic polymers or mixtures thereof; anionic, nonionic, cationic or amphoteric surfactants; pigments; thickeners; antioxidants; penetrants; sequestrants; fragrances; buffers; dispersants; conditioning agents, for instance cations, cationic or amphoteric polymers, chitosans, modified or unmodified, volatile or non-volatile silicones; film-forming agents; ceramides; preserving agents; stabilizers; opacifiers.

Needless to say, a person skilled in the art will take care to select this or these optional additional compound(s) such that the advantageous properties intrinsically associated with the composition in accordance with the invention are not, or are not substantially, adversely affected by the envisaged addition(s).

The above adjuvants are generally present in an amount, for each of them, of between 0 and 20% by weight, relative to the total weight of the composition.

When surfactants are present, use is preferably made of nonionic, anionic or amphoteric surfactants, and preferably alkyl sulfates, alkyl ether sulfates, betaines, imidazolium derivatives, alkylpyrrolidones, oxyalkylenated or glycerolated fatty alkyl ethers, and optionally oxyalkylenated or glycerolated fatty acid esters of monoalcohols or of polyols. More particularly, the content ranges between 0.01% and 30% by weight relative to the total weight of the composition, advantageously between 0.1% and 20% by weight and preferably from 0.2% to 10% by weight relative to the total weight of the composition.

The dye composition according to the invention may be in various forms, such as in the form of liquids, shampoos, creams or gels, or in any other suitable form.

The dye composition is applied to keratin fibres, especially the hair, for a time that is sufficient to develop the desired coloration and optionally the desired lightening, after which the keratin fibres are optionally rinsed, washed with shampoo, rinsed again and dried or left to dry.

The time necessary for development of the coloration on the fibres, especially the hair, may be from about 5 to 60 minutes and more particularly from about 10 to 50 minutes.

The temperature necessary for development of the coloration is generally between room temperature (15 to 25° C.) and 80° C. and more particularly between 15 and 45° C.

Thus, after application of the dye composition according to the invention, it is advantageously possible to subject the head of hair to a heat treatment by heating to a temperature ranging from 15 to 80° C. and preferably between 15 and 45° C., especially to a temperature of 40° C. In practice, this operation may be performed using a hairstyling hood, a hairdryer and other standard heating appliances.

Thus, the dye composition is applied to the keratin fibres at temperatures between room temperature (15 to 25° C.) and 80° C. and more particularly between 15 and 45° C.

In accordance with a first variant according to the present invention, prior to the dyeing process, the keratin fibres undergo a process of permanent reshaping by straightening or relaxing which is performed by means of applying to the said fibres an alkaline cosmetic composition with a pH of at least 10 comprising one or more alkaline agents.

In particular, an alkaline cosmetic composition with a pH of greater than or equal to 10 comprising, in a cosmetically acceptable medium, one or more alkaline agents is applied to the keratin fibres while straightening them, and is left on for the time sufficient for shaping.

The alkaline agent(s) are chosen from alkaline agents of mineral or organic hydroxide type.

Preferably, the alkaline cosmetic composition has a pH ranging from 10 to 14 and even more preferentially from 12 to 14.

The mineral hydroxides may be chosen from alkali metal, alkaline-earth metal and transition metal hydroxides. Examples of mineral hydroxides that may be mentioned include sodium hydroxide, lithium hydroxide, calcium hydroxide, magnesium hydroxide, barium hydroxide, strontium hydroxide, manganese hydroxide and zinc hydroxide.

Among the organic hydroxides, mention may be made of guanidinium hydroxide (or guanidine hydroxide).

Among the mineral hydroxides, sodium hydroxide is preferred.

It should be noted that certain hydroxides, and more particularly guanidine hydroxide, may be in the form of precursors, i.e. of at least two compounds which, when placed in contact, produce guanidine hydroxide via a chemical reaction. By way of example, mention may thus be made of the combination of an alkaline-earth metal hydroxide, for instance calcium hydroxide, with a guanidine carbonate.

Preferably, the mineral or organic hydroxide alkaline agent is chosen from sodium hydroxide and guanidine hydroxide or mixtures thereof.

Advantageously, the content of hydroxide alkaline agent is between 0.5% and 10% by weight and preferably between 1% and 5% by weight relative to the total weight of the composition.

Generally, the medium of this composition comprises water or a mixture of water and of a cosmetically acceptable solvent. The cosmetically acceptable solvents that may be used in the alkaline compositions may correspond to those used in the case of the dye composition.

The solvent content is more particularly not more than 20% by weight relative to the total weight of the alkaline composition.

The alkaline composition may also comprise common additives such as nonionic, anionic, cationic or amphoteric surfactants, and, among these, mention may be made of alkyl sulfates, alkylbenzene sulfates, alkyl ether sulfates, alkylsulfonates, quaternary ammonium salts, alkylbetaines, oxyethylenated alkylphenols, fatty acid alkanolamides, oxyethylenated fatty acid esters, and also other nonionic surfactants of the hydroxypropyl ether type.

When the alkaline composition contains this type of additive, its content is generally less than 30% by weight and preferably between 0.5% and 10% by weight relative to the total weight of the alkaline composition.

The alkaline composition is left on for the time sufficient for shaping.

The leave-on time is generally between 3 and 30 minutes and preferably between 5 and 15 minutes.

The alkaline composition is generally applied at room temperature.

The hair is straightened (or uncurled) generally using a comb. Rinsing may then be performed.

After performing the treatment process of permanent reshaping by straightening or relaxing, the keratin fibres are optionally rinsed.

The treatment may then optionally be neutralized, in particular by applying a shampoo that is capable of neutralizing the alkaline agents used in the alkaline composition.

The keratin fibres may then be washed with a shampoo, rinsed and dried or left to dry.

In accordance with a second variant according to the present invention, prior to the dyeing process, the keratin fibres undergo a permanent reshaping process that is performed by carrying out the following steps:

(i) a reducing composition comprising, in a cosmetically acceptable medium, one or more reducing agents is applied to the keratin fibres and is left on for the time sufficient for shaping, and then (ii) an oxidizing composition is applied for a time sufficient for fixing the shape.

The reducing agents used during step (i) of the permanent reshaping process may be chosen from thiols such as thioglycolic acid and thio lactic acid, salts thereof and esters thereof, cysteine, cysteamine and derivatives thereof, sulfites and bisulfites, especially of alkali metals, of alkaline-earth metals or of ammonium, and mixtures thereof.

The reducing agents may be present in the reducing composition in a content ranging from 0.1% to 20% by weight and preferably in a content ranging from 0.5% to 15% by weight, relative to the total weight of the reducing composition.

Generally, the medium of this composition comprises water or a mixture of water and of one or more cosmetically acceptable solvents. The cosmetically acceptable solvents that may be used in the reducing composition may correspond to those used in the case of the dye composition.

The solvent content is more particularly not more than 20% by weight relative to the total weight of the reducing composition.

The reducing composition may also comprise common additives such as nonionic, anionic, cationic or amphoteric surfactants, and, among these, mention may be made of alkyl sulfates, alkylbenzene sulfates, alkyl ether sulfates, alkylsulfonates, quaternary ammonium salts, alkylbetaines, oxyethylenated alkylphenols, fatty acid alkanolamides, oxyethylenated fatty acid esters, and also other nonionic surfactants of the hydroxypropyl ether type.

When the reducing composition contains this type of additive, its content is generally less than 30% by weight and preferably between 0.5% and 10% by weight relative to the total weight of the reducing composition.

The reducing composition may be in the form of a thickened or unthickened lotion, a cream or a gel, or in any other suitable form.

The leave-on time is generally between 3 and 30 minutes and preferably between 5 and 15 minutes.

The oxidizing composition used in step (ii) of the permanent reshaping process conventionally comprises one or more oxidizing agents, in general aqueous hydrogen peroxide solution, an alkali metal bromate, a persalt or a polythionate, and even more preferentially aqueous hydrogen peroxide solution.

The pH of the oxidizing composition is generally between 2 and 10.

The leave-on time is generally between 3 and 30 minutes and preferably between 5 and 15 minutes.

In particular, the reducing composition is applied to reduce the disulfide bonds of keratin, the keratin fibres being placed under mechanical tension before, during or after the said application.

When it is desired to perform permanent waving, mechanical means are preferably used, such as curlers, in order to place the keratin fibres under tension, the reducing composition being applied before, during or after the hair-shaping means, preferably after.

The reducing composition may be applied to wet hair that has been rolled up beforehand on rollers that are from 2 to 30 mm in diameter. The composition may also be applied gradually as the hair is rolled up. In general, the reducing composition is then left to act for a time of from 5 to 60 minutes and preferably from 5 to 30 minutes.

After applying the reducing composition, the head of hair may also be subjected to a heat treatment by heating to a temperature of between 30 and 250° C. throughout all or part of the leave-on time. In practice, this operation may be performed using a hairstyling hood, a hairdryer, a round or flat iron, an infrared ray dispenser or other standard heating appliances.

It is especially possible to use, both as a heating means and as a means for shaping the head of hair, an iron that heats to a temperature of between 60 and 220° C. and preferably between 120 and 200° C., the use of the heating iron taking place after the intermediate rinsing step following the application of the reducing composition.

The curler itself may be a heating means.

The oxidizing composition for reforming the disulfide bonds of keratin is then applied to the rolled up or unrolled hair, generally for a leave-on time of 2 to 15 minutes.

In the case of a hair uncurling or relaxing process, the reducing composition is applied to the hair, and the hair is then subjected to mechanical reshaping for fixing the hair in its new shape, by means of a hair straightening operation, with a large-toothed comb, with the back of a comb, by hand or with a brush. A leave-on time of from 5 to 60 minutes and preferably from 15 to 45 minutes is generally implemented.

This application may also be followed with a heating treatment, especially using an iron.

The straightening of the hair may also be performed, totally or partly, using a heating iron at between 60 and 220° C. and preferably between 120 and 200° C.

The oxidizing composition as defined above is then applied, and is generally left to act for about 2 to 15 minutes, and the hair is then optionally rinsed thoroughly, generally with water.

After performing the permanent reshaping treatment process, the keratin fibres are optionally rinsed.

Preferably, the keratin fibres impregnated with the oxidizing composition are rinsed thoroughly with water. The keratin fibres may optionally be separated, before or after, from the means needed to keep them under tension.

The keratin fibres may then be washed with a shampoo, rinsed and dried or left to dry.

Preferably, a treatment serving to form a complex with the natural dye(s) used in the dye composition is performed on the keratin fibres, between steps d) and g) of the dyeing process according to the invention.

In particular, once the keratin fibres have been subjected to a permanent reshaping process by straightening or relaxing, a treatment of the fibres based on one or more metal salts that are capable of forming a complex with the natural dyes used in step e) of the dyeing process may be performed.

In other words, a complexation treatment of the natural dyes that are used in step e) of the dyeing process may be performed.

Thus, the treatment serving to form a complex with the natural dyes consists in applying to the keratin fibres a cosmetic composition comprising, in a cosmetically acceptable medium, one or more metal salts, in particular one or more zinc (Zn) salts.

Preferably, the cosmetic composition comprising one or more zinc (Zn) salts is applied to the keratin fibres between steps d) and e) of the dyeing process according to the invention, and thus before the application of the dye composition.

In other words, the cosmetic composition containing one or more zinc (Zn) salts constitutes a pretreatment or post-treatment for the complexation of the natural dyes before the application of the dye composition.

The zinc salts used in this cosmetic composition may be of organic or mineral nature.

When the zinc salt is an organic acid, it may contain one or more carboxylic acid (—COOH) and/or sulfonic acid (—SO$_3$H) and/or phosphonic acid (—H$_2$PO$_3$) and/or phosphinic acid (—H$_2$PO$_2$ or =HPO$_2$) and/or phosphinous acid (=POH) functions.

Preferably, the organic acid according to the invention contains one or more carboxylic and/or sulfonic acid functions.

The organic acid according to the invention may be saturated or unsaturated, and linear, branched or cyclic.

The organic acid zinc salt according to the invention may be chosen especially from zinc gluconate, zinc lactate, zinc glycinate, zinc aspartate, zinc pyrrolidonecarboxylate (more commonly known as zinc pido late), zinc phenolsulfonate, zinc salicylate, zinc citrate and zinc acetate, and mixtures thereof.

For the purposes of the present invention, the term "mineral salts" means inorganic salts, i.e. salts not comprising in their structure any carbon atoms bonded to at least one hydrogen atom. The mineral salts are salts derived from the action of a mineral acid or a mineral base on zinc.

Among the salts, mention may be made of zinc halides such as chloride, fluoride and iodide; zinc sulfate, phosphate, nitrate, carbonate or perchlorate, and also mixtures thereof.

Preferably, the zinc mineral salts used are zinc sulfate, zinc phosphate and zinc chloride.

The zinc mineral salts may be introduced in solid form into the compositions or may be derived from a natural, mineral or spring water that is rich in these ions or alternatively from seawater (especially the Dead Sea). They may also originate from mineral compounds, for instance earths, rocks, ochres such as clays (for example green clay) or even from a plant extract containing them, as described, for example in patent FR 2 814 943.

As mineral rocks containing zinc salts, mention may be made of the following rocks:

| | |
|---|---|
| Boyleite | $(ZnMg)SO_4$—$4H_2O$ |
| Changoite | $Na_2Zn(SO_4)_2$—$4H_2O$ |
| Clinohedrite | $CaZn[SiO_4]$—$H_2O$ |
| Gaultite | $Na_4Zn_2Si_7O_{18}$—$5H_2O$ |
| Goslarite | $ZnSO_4$—$7H_2O$ |
| Hardystonite | $Ca_2Zn[Si_2O_7]$ |
| Hopeite | $Zn_3(PO_4)_2$—$4H_2O$ |
| Hydrozincite | $Zn_5[(OH)_3|CO_3]_2$ |
| IMA2008-048 | $Zn_6(PO_4)_4$—$7H_2O$ |
| Minrecordite | $CaZn(CO_3)_2$ |
| Osakaite | $Zn_4(SO_4XOH)_6$—$5H_2O$ |
| Parahopeite | $Zn_3(PO_4)_2$—$4H_2O$ |
| Parascholzite | $CaZn_2(PO_4)_2$—$2H_2O$ |
| Scholzite | $CaZn_2(PO_4)_2$—$2H_2O$ |
| Simonkolleite | $Zn_5[(OH)_8|Cl_2]$—$H_2O$ |
| Skorpionite | $Ca_3Zn_2[(OH)_2|CO_3|(PO_4)_2]$—$H_2O$ |
| Smithsonite | $ZnCO_3$ |
| Spencerite | $Zn_4[OH|PO_4]_2$—$3H_2O$ |
| Tarbuttite | $Zn_2[OH|PO_4]$ |
| Basic Zinc Sulfate Hydrate | $Zn_4SO_4(OH)_6$—$4H_2O$ |
| Willemite | $Zn_2[SiO_4]$ |
| Zincsilite | $Zn_3Si_4O_{10}(OH)_2$—$4H_2O$ |
| Zinkosite | $ZnSO_4$ |

In particular, the zinc salts of the invention are of oxidation state 2: Zn(II).

Even more preferentially, the zinc salts are chosen from zinc gluconate, zinc citrate, zinc glycinate, zinc phosphate, zinc sulfate and zinc chloride.

In particular, the zinc salt used in the cosmetic composition is zinc glycinate.

Preferably, the composition according to the invention comprises from 0.1% to 5% by weight and preferably from 0.1% to 3% by weight of zinc salts relative to the total weight of the composition containing them.

The cosmetic composition containing one or more zinc salts may also contain one or more aromatic alcohols as described previously in the context of the dye composition.

In particular, the cosmetic composition contains a benzyl alcohol.

Generally, the medium of this composition comprises water or a mixture of water and of a cosmetically acceptable solvent. The cosmetically acceptable solvents that may be used in this composition may correspond to those used in the case of the dye composition.

In particular, the cosmetic composition comprises ethanol.

Furthermore, the cosmetic composition may contain one or more thickeners, especially one or more nonionic thickeners preferably chosen from thickening polysaccharides such as carrageenans.

The cosmetic composition containing one or more zinc salts may be applied to the keratin fibres, especially the hair, for a time from about 5 to 20 minutes, more particularly 5 to 15 minutes and especially 10 minutes.

The cosmetic composition containing such zinc salts may be applied at room temperature (15 to 25° C.).

Preferably, the keratin fibres are rinsed after the application of the cosmetic composition containing the zinc salt(s).

According to one preferred embodiment, the dyeing process according to the invention comprises the following steps:
an alkaline cosmetic composition whose pH is greater than at least 10 comprising one or more alkaline agents of mineral or organic hydroxide type is applied,
the alkaline agent(s) used in the straightening or relaxing treatment are neutralized by applying a shampoo, and the fibres are then rinsed,
a cosmetic composition comprising one or more metal salts that are capable of forming a complex with one or more natural dyes subsequently used, in particular one or more organic acid zinc salts, is applied to the said fibres,
the said fibres are rinsed,
at least one dye composition comprising, in a cosmetically acceptable medium, one or more natural dyes, in particular those chosen from curcumin, chlorophylline, haematoxylin, haematin, brazileine, brazilin and laccaic acid, and mixtures thereof, is applied to the said fibres,
the keratin fibres are optionally rinsed and washed with shampoo,
the keratin fibres are optionally dried.

According to another preferred embodiment, the dyeing process according to the invention comprises the following steps:
a) a reducing composition comprising one or more reducing agents is applied to the keratin fibres and then
b) an oxidizing composition is applied for a time sufficient for fixing the shape,
c) the said fibres are rinsed,
c') a cosmetic composition comprising one or more metal salts that are capable of forming a complex with one or more natural dyes used in step e), in particular one or more organic acid zinc salts, is applied to the said fibres,
d') the said fibres are rinsed,
e) a dye composition comprising, in a cosmetically acceptable medium, one or more natural dyes, in particular those chosen from curcumin, chlorophylline, haematoxylin, haematin, brazileine, brazilin and laccaic acid, and mixtures thereof, is applied to the said fibres,
f) the keratin fibres are optionally rinsed and washed with shampoo,
g) the keratin fibres are optionally dried.

The examples that follow serve to illustrate the invention without, however, being limiting in nature.

EXAMPLES

Example I

Permanent Reshaping by Alkaline Relaxing Followed by Dyeing

1. Compositions Tested

The dye compositions (A) and (B) below are prepared from the ingredients indicated in the table below. The amounts mentioned are indicated in grams of active material.

| | Compositions | |
|---|---|---|
| | A | B |
| Bentonite | 6 g | — |
| Laponite | — | 3.5 g |
| Benzyl alcohol | 1 g | 5 g |
| Cocoglucoside | 2 g | — |
| Ethanol | — | 15 g |
| Extract of *Haematoxylon campechianum* | 4 g (=about 0.4 g of haematin) | 4 g (=about 0.4 g of haematin) |
| Curcumin | 1.5 g | — |
| Chlorophylline | 1 g | — |
| Water | qs 100 g | qs 100 g |

2. Procedure 2.1. Procedure—Relaxing

First, an alkaline relaxing product sold under the name Dark and Lovely Super by the company L'Oréal Professionnel (containing 4.83% by weight of guanidine hydroxide) at pH 12.5 is applied for 15 minutes to locks of natural Caucasian, Chinese and Indian grey hair containing 90% white hairs. After the application of a neutralizing shampoo, the locks are rinsed.

2.2. Procedure—Complexing Pretreatment

Prior to the application of the dye composition (A), a complexing pretreatment with zinc is performed using the cosmetic composition (C), the ingredients of which are indicated in the table below. The amounts mentioned are indicated in grams of active material.

|  | Composition C |
|---|---|
| Carrageenan | 1.5 g |
| Zinc glycinate | 3.3 g |
| Benzyl alcohol | 5 g |
| Ethanol | 15 g |
| Water | qs 100 g |

To do this, composition (C) is applied to the locks at room temperature. After a leave-on time of 10 minutes, the locks are rinsed.

In the case of dyeing performed by means of the dye composition (B), the cosmetic composition (C) is not applied to the locks.

2.3. Procedure—Dyeing

Finally, the dye compositions (A) and (B) are respectively applied to the locks at a temperature of 40° C. After a leave-on time of 45 minutes, the locks are rinsed, washed with a shampoo and dried.

3. Colorimetric Results

The colour of the locks was evaluated in the CIE L* a* b* system, using a Minolta Spectrophotometer CM2600D colorimeter. In this L* a* b* system, the three parameters denote, respectively, the colour intensity (L*), the green/red colour axis (a*) and the blue/yellow colour axis (b*). The smaller the value of L*, the stronger the coloration obtained.

The variation in coloration between the locks of untreated natural Caucasian, Chinese or Indian grey hair containing 90% white hairs (control) and the locks after coloration are defined by (ΔE*) according to the following equation:

$$\Delta E^* = \sqrt{(L^* - L_o^*)^2 + (a^* - a_o^*)^2 + (b^* - b_o^*)^2}$$

In this equation, L*, a* and b* represent the values measured on locks of hair after dyeing and $L_o^*$, $a_o^*$ and $b_o^*$ represent the values measured on locks of untreated undyed hair, i.e. on the undyed Caucasian, Chinese or Indian hair. The higher the ΔE* value, the better the colour uptake is.

The colour build-up ΔE* and the luminance L* values are given in the tables below:

i) Caucasian Hair

|  | $L^*_o$ | $a^*_o$ | $b^*_o$ | ΔE* |
|---|---|---|---|---|
| Undyed Caucasian hair | 61.19 | 0.97 | 12.47 | — |

|  | L* | a* | b* | ΔE* |
|---|---|---|---|---|
| Caucasian hair dyed with A | 19.01 | 2.07 | −0.93 | 44.27 |
| Caucasian hair dyed with B | 21.37 | 7.36 | 3.73 | 41.27 | ii) Chinese Hair

|  | $L^*_o$ | $a^*_o$ | $b^*_o$ | ΔE* |
|---|---|---|---|---|
| Undyed Chinese hair | 72.2 | 1.26 | 21.2 | — |

|  | L* | a* | b* | ΔE* |
|---|---|---|---|---|
| Chinese hair dyed with A | 18.35 | 2.04 | −1.03 | 58.26 |
| Chinese hair dyed with B | 22.94 | 7.89 | 4.09 | 52.57 | iii) Indian Hair

|  | $L^*_o$ | $a^*_o$ | $b^*_o$ | ΔE* |
|---|---|---|---|---|
| Undyed Indian hair | 56.3 | 1.67 | 15.42 | — |

|  | L* | a* | b* | ΔE* |
|---|---|---|---|---|
| Indian hair dyed with A | 18.73 | 1.86 | −0.52 | 40.81 |
| Indian hair dyed with B | 21.11 | 6.44 | 2.89 | 37.66 |

It is found that strong colorations are obtained on the locks of hair irrespective of the nature of the hair used. In particular, a very strong black coloration is obtained for the locks treated with the dye composition (A) and a very strong violet coloration is obtained for the locks treated with the dye composition (B).

Moreover, grey hair is satisfactorily covered with the dye compositions according to the invention.

It is also found that the colorations are very fast with respect to shampooing and to ultraviolet rays.

Example II

Permanent-Waving Followed by Dyeing

1. Compositions Tested

The dye compositions (A) and (B) below are prepared from the ingredients indicated in the table below. The amounts mentioned are indicated in grams of active material.

|  | Compositions | |
|---|---|---|
|  | A | B |
| Bentonite | 6 g | — |
| Laponite | — | 3.5 g |
| Benzyl alcohol | 1 g | 5 g |
| Cocoglucoside | 2 g | — |
| Ethanol | — | 15 g |
| Extract of *Haematoxylon campechianum* | 4 g (=about 0.4 g of haematin) | 4 g (=about 0.4 g of haematin) |
| Curcumin | 1.5 g | — |
| Chlorophylline | 1 g | — |
| Water | qs 100 g | qs 100 g |

2. Procedure 2.1. Procedure—Permanent-Waving

First, a reducing composition sold under the name Dulcia Vital Force DV2 (11.36% by weight of ammonium dithioglycolate at pH 8.4) by the company L'Oréal Professionnel is applied to locks of natural Caucasian, Chinese and Indian grey hair containing 90% white hairs. After a leave-on time of 20 minutes, a fixing composition (2.4% by weight of $H_2O_2$ at pH 3) is applied to the locks as a whole.

After a leave-on time of 10 minutes, the locks are rinsed.

2.2. Procedure—Complexing Pretreatment

Prior to the application of the dye composition (A), a complexing pretreatment with zinc is performed using the cosmetic composition (C), the ingredients of which are indicated in the table below. The amounts mentioned are indicated in grams of active material.

|  | Composition C |
| --- | --- |
| Carrageenan | 1.5 g |
| Zinc glycinate | 3.3 g |
| Benzyl alcohol | 5 g |
| Ethanol | 15 g |
| Water | qs 100 g |

To do this, composition (C) is applied to the locks at room temperature. After a leave-on time of 10 minutes, the locks are rinsed.

In the case of dyeing performed by means of the dye composition (B), the cosmetic composition (C) is not applied to the locks.

2.3. Procedure—Dyeing

Finally, the dye compositions (A) and (B) are respectively applied to the locks at a temperature of 40° C. After a leave-on time of 45 minutes, the locks are rinsed, washed with a shampoo and dried.

3. Colorimetric Results

The colour of the locks was evaluated in the CIE L* a* b* system, using a Minolta Spectrophotometer CM2600D colorimeter. In this L* a* b* system, the three parameters denote, respectively, the colour intensity (L*), the green/red colour axis (a*) and the blue/yellow colour axis (b*). The smaller the value of L*, the stronger the coloration obtained.

The variation in coloration between the locks of untreated natural Caucasian, Chinese or Indian grey hair containing 90% white hairs (control) and the locks after coloration are defined by ($\Delta E^*$) according to the following equation:

$$\Delta E^* = \sqrt{(L^*-L_o^*)^2 + (a^*-a_o^*)^2 + (b^*-b_o^*)^2}$$

In this equation, L*, a* and b* represent the values measured on locks of hair after dyeing and $L_o^*$, $a_o^*$ and $b_o^*$ represent the values measured on locks of undyed untreated hair. The higher the $\Delta E^*$ value, the better the colour uptake is.

The colour build-up $\Delta E^*$ and the luminance L* values are given in the tables below:

i) Caucasian Hair

|  | $L^*_o$ | $a^*_o$ | $b^*_o$ | $\Delta E^*$ |
| --- | --- | --- | --- | --- |
| Undyed Caucasian hair | 61.19 | 0.97 | 12.47 | — |

|  | L* | a* | b* | $\Delta E^*$ |
| --- | --- | --- | --- | --- |
| Caucasian hair dyed with A | 20.65 | 3.21 | −2.42 | 43.25 |
| Caucasian hair dyed with B | 27.05 | 15.86 | 13.65 | 37.26 | ii) Chinese Hair

|  | $L^*_o$ | $a^*_o$ | $b^*_o$ | $\Delta E^*$ |
| --- | --- | --- | --- | --- |
| Undyed Chinese hair | 72.2 | 1.26 | 21.2 | — |

|  | L* | a* | b* | $\Delta E^*$ |
| --- | --- | --- | --- | --- |
| Chinese hair dyed with A | 22.15 | 3.56 | −3.06 | 55.67 |
| Chinese hair dyed with B | 35.41 | 17.26 | 19.88 | 40.14 | iii) Indian Hair

|  | $L^*_o$ | $a^*_o$ | $b^*_o$ | $\Delta E^*$ |
| --- | --- | --- | --- | --- |
| Undyed Indian hair | 56.3 | 1.67 | 15.42 | — |

|  | L* | a* | b* | $\Delta E^*$ |
| --- | --- | --- | --- | --- |
| Indian hair dyed with A | 19.97 | 2.36 | −1.77 | 40.2 |
| Indian hair dyed with B | 29.13 | 15.66 | 14.78 | 30.57 |

It is found that strong colorations are obtained on the locks of hair irrespective of the nature of the hair used. In particular, a very strong black coloration is obtained for the locks treated with the dye composition (A) and a very strong brown coloration is obtained for the locks treated with the dye composition (B).

Moreover, grey hair is satisfactorily covered with the dye compositions according to the invention.

Furthermore, chromatic colorations are obtained for the locks treated with the dye composition (B).

It is also found that the colorations are very fast with respect to shampooing and to ultraviolet rays.

Example III

Straightening/Dyeing

1. Compositions Tested

The dye compositions (A) and (B) described in Examples I and II are used.

2. Procedure—Straightening

First, a straightening product sold under the name XTenso Moisturist (containing 4% by weight of cysteine at pH 9.3) by the company L'Oréal is applied to locks of natural Caucasian, Chinese and Indian grey hair containing 90% white hairs. After a leave-on time of 20 minutes, a fixing composition (2.4% by weight of $H_2O_2$ at pH 2.5) is applied to the locks as a whole.

After a leave-on time of 10 minutes, the locks are rinsed.

2.2. Procedure—Complexing Pretreatment

Prior to the application of the dye composition (A), a complexing pretreatment with zinc is performed using the cosmetic composition (C) described in Examples 1 and 2.

To do this, composition (C) is applied to the locks at room temperature. After a leave-on time of 10 minutes, the locks are rinsed.

In the case of dyeing performed by means of the dye composition (B), the cosmetic composition (C) is not applied to the locks.

2.3. Procedure—Dyeing

Finally, the dye compositions (A) and (B) are respectively applied to the locks at a temperature of 40° C. After a leave-on time of 45 minutes, the locks are rinsed, washed with a shampoo and dried.

3. Colorimetric Results

The variation in coloration ($\Delta E^*$) between the locks of untreated natural Caucasian, Chinese or Indian grey hair containing 90% white hairs (control) and the locks after coloration are evaluated according to the equation mentioned hereinabove.

The results are collated in the following tables:

i) Caucasian Hair

|  | $L^*_0$ | $a^*_0$ | $b^*_0$ | $\Delta E^*$ |
|---|---|---|---|---|
| Undyed Caucasian hair | 61.19 | 0.97 | 12.47 | — |

|  | $L^*$ | $a^*$ | $b^*$ | $\Delta E^*$ |
|---|---|---|---|---|
| Caucasian hair dyed with A | 16.59 | 2.74 | −1.12 | 46.66 |
| Caucasian hair dyed with B | 23.31 | 11.39 | 6.12 | 39.8 | ii) Chinese Hair

|  | $L^*_0$ | $a^*_0$ | $b^*_0$ | $\Delta E^*$ |
|---|---|---|---|---|
| Undyed Chinese hair | 72.2 | 1.26 | 21.2 | — |

|  | $L^*$ | $a^*$ | $b^*$ | $\Delta E^*$ |
|---|---|---|---|---|
| Chinese hair dyed with A | 18.79 | 2.61 | −1.37 | 58 |
| Chinese hair dyed with B | 25.09 | 16.45 | 9.86 | 50.78 | iii) Indian Hair

|  | $L^*_0$ | $a^*_0$ | $b^*_0$ | $\Delta E^*$ |
|---|---|---|---|---|
| Undyed Indian hair | 56.3 | 1.67 | 15.42 | — |

|  | $L^*$ | $a^*$ | $b^*$ | $\Delta E^*$ |
|---|---|---|---|---|
| Indian hair dyed with A | 18.15 | 1.99 | −1.04 | 41.55 |
| Indian hair dyed with B | 21.29 | 11.34 | 5.78 | 37.58 |

It is found that strong colorations are obtained on the locks of hair irrespective of the nature of the hair used. In particular, a very strong black coloration is obtained for the locks treated with the dye composition (A) and a very strong mahogany coloration is obtained for the locks treated with the dye composition (B).

Moreover, grey hair is satisfactorily covered with the dye compositions according to the invention.

It is also found that the colorations are very fast with respect to shampooing and to ultraviolet rays.

The invention claimed is:

1. Process for dyeing keratin fibres, in particular human keratin fibres in which:
    a) an aqueous alkaline composition comprising one or more alkaline agents in an amount such that the pH of the composition is greater than at least 10 is applied to the said fibres, or a reducing composition comprising one or more reducing agents and then an oxidizing composition are applied to the said fibres,
    b) the said fibres are optionally rinsed,
    c) optionally, the treatment is neutralized, and the fibres are washed with shampoo and rinsed,
    d) optionally, the fibres are dried or left to dry,
    e) a dye composition comprising, in a cosmetically acceptable medium, one or more natural dyes is applied to the said fibres,
    f) optionally, the fibres are washed and rinsed,
    g) the fibres are dried or left to dry.

2. Dyeing process according to claim 1, characterized in that the natural dyes are chosen from lawsone and henna, curcumin, alizarin, purpurin, purpurogallin, indigo, Tyrian purple, chlorophylline, sorghum, kermesic acid, carminic acid, catechin, epicatechin, juglone, bixin, betanin, quercetin, chromene dyes and chroman dyes, and laccaic acids.

3. Dyeing process according to claim 1, characterized in that the natural dyes are chosen from chromene dyes and chroman dyes.

4. Dyeing process according to claim 1, characterized in that the natural dyes are chosen from the compounds having the following formulae:
    formula (I):

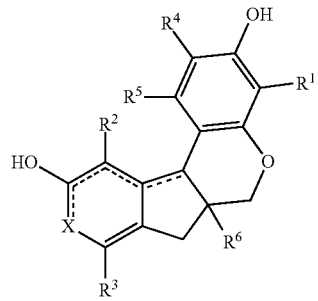

in which:
    ---- represents a carbon-carbon single bond or a carbon-carbon double bond, the sequence of these bonds ----- denotes two carbon-carbon single bonds and two carbon-carbon double bonds, the said bonds being conjugated, X represents a group:

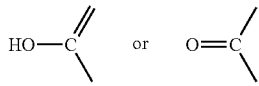

$R^1$, $R^2$, $R^3$, $R^4$, $R^5$ and $R^6$, which may be identical or different, represent, independently of each other, a hydrogen atom, a hydroxyl group, an optionally substituted alkyl group, an optionally substituted alkoxy group or an optionally substituted acyloxy group, and also the tautomeric and/or mesomeric forms thereof, the stereoisomers thereof, the addition salts thereof with a cosmetically acceptable acid or base, and the hydrates thereof, and formula (II):

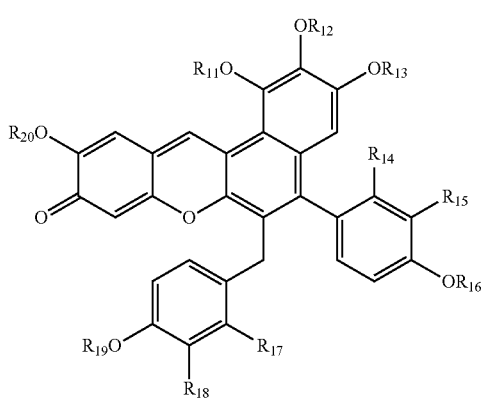

(II)

in which:

$R_{11}$, $R_{12}$, $R_{13}$, $R_{16}$, $R_{19}$ and $R_{20}$, which may be identical or different, represent, independently of each other, a hydrogen atom or a $C_1$-$C_4$ alkyl radical, $R_{14}$, $R_{15}$, $R_{17}$ and $R_{18}$, which may be identical or different, represent, independently of each other, a hydrogen atom, a hydroxyl radical or a $C_1$-$C_4$ alkoxy radical, and also the tautomeric and/or mesomeric forms thereof, the stereoisomers thereof, the addition salts thereof with a cosmetically acceptable acid or base, and the hydrates thereof.

5. Process according to claim 1, characterized in that the natural dyes are chosen from laccaic acids.

6. Process according to claim 5, characterized in that the natural dyes are chosen from the compounds of formula (III) below:

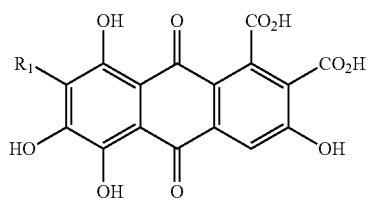 [SMILES: Cc1c(O)c(O)c2c(c1O)C(=O)c1c(cc(O)c(C(=O)O)c1C(=O)O)C2=O]

(III)

$R_1$ denoting a phenyl radical substituted with at least one hydroxyl group, and preferably with a hydroxyl group that is advantageously in the ortho position relative to the bond attaching it to the fused rings.

7. Process according to claim 1, characterized in that the natural dyes are chosen from haematin and brazileine, and mixtures thereof.

8. Process according to claim 1, characterized in that the dye composition also comprises one or more aromatic alcohols, in particular those chosen from benzyl alcohol, phenylethanol and phenylpropanol.

9. Process according to claim 1, characterized in that the dye composition also comprises one or more oxidizing agents.

10. Process according to claim 1, characterized in that the dye composition comprises one or more hydrophilic or organophilic clays.

11. Process according to claim 1, characterized in that the dye composition is applied to the keratin fibres at temperatures between 15 and 80° C.

12. Process according to claim 1, characterized in that the alkaline agents used in the alkaline composition are chosen from alkaline agents of mineral or organic hydroxide type.

13. Process according to claim 12, characterized in that the alkaline agents of mineral or organic hydroxide type are chosen from sodium hydroxide and guanidine hydroxide, or mixtures thereof.

14. Process according to claim 1, characterized in that the reducing composition is applied to reduce the disulfide bonds of keratin, the keratin fibres being placed under mechanical tension before, during or after the said application.

15. Process according to claim 1, characterized in that a treatment serving to form a complex with the natural dye(s) used in the dye composition is performed between steps d) and g) of the process.

16. Process according to claim 1, characterized in that a cosmetic composition containing, in a cosmetically acceptable medium, one or more zinc salts is applied to the keratin fibres between steps d) and g), in particular between steps d) and e) of the process.

17. Process according to claim 16, characterized in that the zinc salt(s) are chosen from zinc gluconate, zinc citrate, zinc acetate, zinc lactate, zinc glycinate, zinc aspartate, zinc pyrrolidonecarboxylate, zinc phenolsulfonate and zinc salicylate, and also mixtures thereof.

* * * * *